(12) United States Patent
Bolinger et al.

(10) Patent No.: US 8,271,208 B1
(45) Date of Patent: Sep. 18, 2012

(54) FLAME IONIZATION DETECTOR MANAGEMENT SYSTEM

(75) Inventors: Jeremy Bolinger, League City, TX (US); Kevin Moses, League City, TX (US)

(73) Assignee: LDARtools, Inc., League City, TX (US)

( * ) Notice: Subject to any disclaimer, the term of this patent is extended or adjusted under 35 U.S.C. 154(b) by 251 days.

(21) Appl. No.: 12/474,504

(22) Filed: May 29, 2009

Related U.S. Application Data (60) Provisional application No. 61/057,124, filed on May 29, 2008.

(51) Int. Cl.
  *G01D 18/00* (2006.01)
  *G01N 31/00* (2006.01)
(52) U.S. Cl. .............................. 702/24; 702/85; 702/23
(58) Field of Classification Search .................... 702/24, 702/85, 23; 324/464
  See application file for complete search history.

(56) References Cited

U.S. PATENT DOCUMENTS

| | | |
|---|---|---|
| 3,853,455 A | 12/1974 | Riordan et al. |
| 3,985,509 A | 10/1976 | Trone et al. |
| 4,346,055 A | 8/1982 | Murphy et al. |
| H572 H | 2/1989 | Hansen |
| 5,206,818 A | 4/1993 | Speranza |
| 5,356,594 A | 10/1994 | Neel et al. |
| 6,341,287 B1 | 1/2002 | Sziklai et al. |
| 6,438,535 B1 | 8/2002 | Benjamin et al. |
| 6,478,849 B1 | 11/2002 | Taylor et al. |
| 6,545,278 B1 | 4/2003 | Mottier et al. |
| 6,609,090 B1 | 8/2003 | Hickman et al. |
| 6,672,129 B1 | 1/2004 | Frederickson et al. |
| 6,680,778 B2 | 1/2004 | Hinnrichs et al. |
| 6,722,185 B2 | 4/2004 | Lawson et al. |
| 7,017,386 B2 | 3/2006 | Liu et al. |
| 7,103,610 B2 | 9/2006 | Johnson et al. |
| 7,136,904 B2 | 11/2006 | Bartek et al. |
| 7,369,945 B2 | 5/2008 | Miller et al. |
| 7,588,726 B1 | 9/2009 | Mouradian et al. |
| 7,657,384 B1 | 2/2010 | Moses |

(Continued)

FOREIGN PATENT DOCUMENTS
WO 2006-022648 A1 3/2006

OTHER PUBLICATIONS

*Environmental Analytics, Inc. v. TMX2, Inc. and LDAR Solutions, Ltd.*; Case 4:08-cv-03353; USDC, Southern District of Texas; First Amended Complaint; Dec. 10, 2008.

(Continued)

*Primary Examiner* — Mohamed Charioui
*Assistant Examiner* — Manuel Rivera Vargas
(74) *Attorney, Agent, or Firm* — Pramudji Law Group PLLC; Ari Pramudji (57) ABSTRACT

A method for calibrating a flame ionization detector (FID). The method includes receiving a request to schedule a calibration. After scheduling the calibration, a flow request command is sent to a gas distribution system at a scheduled calibration. The flow request command instructs the gas distribution system to provide a gas at a gas concentration level to the FID. After the gas distribution system provides the gas at the gas concentration level to the FID, the method includes receiving a raw count from the FID and correlating the raw count with the gas and the gas concentration level provided to the FID. The method then stores the results of the correlation in a calibration log.

42 Claims, 5 Drawing Sheets

U.S. PATENT DOCUMENTS

| | | | |
|---|---|---|---|
| 7,840,366 B1 * | 11/2010 | Moses et al. | 702/85 |
| 2002/0026339 A1 | 2/2002 | Frankland et al. | |
| 2002/0080032 A1 | 6/2002 | Smith et al. | |
| 2002/0094498 A1 | 7/2002 | Rodriguez-Rodriguez et al. | |
| 2003/0012696 A1 | 1/2003 | Millancourt | |
| 2003/0081214 A1 | 5/2003 | Mestha et al. | |
| 2003/0085714 A1 * | 5/2003 | Keyes et al. | 324/464 |
| 2004/0226345 A1 | 11/2004 | McCoy et al. | |
| 2004/0258213 A1 | 12/2004 | Beamon et al. | |
| 2005/0000981 A1 | 1/2005 | Peng et al. | |
| 2005/0053104 A1 | 3/2005 | Kulp et al. | |
| 2005/0117641 A1 | 6/2005 | Xu et al. | |
| 2005/0262995 A1 | 12/2005 | Kilkis | |
| 2006/0020186 A1 | 1/2006 | Brister et al. | |
| 2006/0220688 A1 | 10/2006 | Germouni et al. | |
| 2006/0235611 A1 | 10/2006 | Deaton et al. | |
| 2006/0286945 A1 | 12/2006 | Reznik et al. | |
| 2007/0000310 A1 | 1/2007 | Yamartino et al. | |
| 2008/0021717 A1 | 1/2008 | Kaartinen et al. | |
| 2008/0063298 A1 | 3/2008 | Zhou et al. | |
| 2008/0092625 A1 | 4/2008 | Hinnrichs | |
| 2008/0120043 A1 | 5/2008 | Miller et al. | |
| 2008/0231719 A1 | 9/2008 | Benson et al. | |
| 2009/0315669 A1 * | 12/2009 | Lang et al. | 340/3.1 |

OTHER PUBLICATIONS

"2nd Annual Fugitive Emissions—Leak Detection and Repair Symposium"; ISA Technical Conference Brochure; Nov. 2002.

"Introducing the Allegro CX(TM) Field Computer"; Product Newswire (product announcement); Jun. 21, 2004.

"New from Accutech, Wireless Acoustic Monitor Field Units Make Fugitive Emissions Monitoring Compliance Easy"; Product Announcement/Description; Feb. 10, 2004.

"LDARManager™ Makes Fugitive Emission Monitoring a Breeze TISCOR launches its newest product for Leak Detection and Repair"; product announcement/description; Nov. 8, 2002.

Office Action (Aug 4, 2009); U.S. Appl. No. 12/032,499 (Moses, et al).

Response/Amendment After Final (Aug. 24, 2010); Final Office Action (Jun. 25, 2010); Response to Office Action (Apr. 26, 2010); and Office Action (Jan. 25, 2010); U.S. Appl. No. 11/668,367 (Skiba, et al).

Response to Office Action (Jul. 13, 2010); Office Action (Apr. 14, 2010); Response/Amendment After Final (Mar. 29, 2010); Final Office Action (Jan. 29, 2010); Response to Office Action (Nov. 4, 2009); and Office Action (Aug. 4, 2010); U.S. Appl. No. 12/032,499 (Moses, et al).

Office Action (Sep. 27, 2010); U.S. Appl. No. 12/133,920 (Moses, et al).

Response to Office Action (Mar. 21, 2011), Office Action (Dec. 21, 2010), RCE (Sep. 27, 2010), Advisory Action (Sep. 10, 2010); U.S. Appl. No. 11/668,367 (Skiba, et al).

Response After Final (May 23, 2011), Final Office Action (Mar. 22, 2011), Response to Office Action (Dec. 27, 2010); U.S. Appl. No. 12/133,920 (Moses, et al).

"Bluetooth Tutorial—Specifications"; Palo Wireless: Bluetooth Resource Center [online]; Jan. 5, 2006; retrieved Dec. 23, 2009 via Internet Archive Wayback Machine.

Response to Office Action (Feb. 21, 2012) and USPTO Office Action (Nov. 18, 2011); U.S. Appl. No. 12/359,196 (Moses, et al.).

* cited by examiner

FLAME IONIZATION DETECTOR MANAGEMENT SYSTEM

RELATED APPLICATIONS

This application claims priority to U.S. provisional patent application Ser. No. 61/057,124, filed May 29, 2008, titled BATTERY OPERATED FLAME IONIZATION DETECTOR, which is incorporated herein by reference.

BACKGROUND

1. Field of the Invention

Implementations of various technologies described herein are directed to flame ionization detectors (FIDs) and to various methods and/or systems for managing and calibrating the FIDs.

2. Description of the Related Art

The following descriptions and examples do not constitute an admission as prior art by virtue of their inclusion within this section.

Industrial plants that handle volatile organic compounds (VOCs) sometimes experience unwanted emissions of those compounds into the atmosphere from point sources, such as smokestacks, and non-point sources, such as valves, pumps, and/or vessels containing the VOCs. Emissions from non-point sources typically occur due to leakage of the VOCs from joints and/or seals and may be referred to herein as "fugitive emissions". Fugitive emissions from control valves typically occur as leakage through the packing set around the valve stem. Control valves used in demanding service conditions involving large temperature fluctuations and frequent movements of the valve stem commonly suffer accelerated deterioration of the valve stem packing set.

The United States Environmental Protection Agency (EPA) has promulgated regulations specifying a maximum permitted leakage of certain hazardous air pollutants, such as benzene, toluene, 1,1,1-trichloroethane, from certain hardware or fixtures, e.g., control valves. Fugitive emissions are typically monitored using a VOC detector, like a FID, which may also be referred to as a vapor analyzer. Government regulations require that VOC detectors used in the testing of valves and other components in petrochemical processing or manufacturing facilities be calibrated at various intervals. These calibration activities must be documented and made available for inspection for up to five years. If the calibrations are not performed, or if they are performed but not documented, the facility owner can be fined and/or suffer other regulatory sanctions.

SUMMARY

Described herein are implementations of various technologies for automatically managing the calibration and validation of a flame ionization detector (FID). In one implementation, managing the calibration of a FID may include a method for calibrating a flame ionization detector (FID). The method begins by receiving a request to schedule a calibration. After receiving the calibration schedule request, the method may send a flow request command to a gas distribution system at a scheduled calibration. The flow request command may instruct the gas distribution system to provide a gas at a gas concentration level to the FID. After the gas distribution system provides the gas at the gas concentration level to the FID, the method may include receiving a raw count from the FID and correlating the raw count with the gas and the gas concentration level provided to the FID. The method may then store the results of the correlation in a calibration log.

In another implementation, managing the calibration of the FID may include a method for determining whether a calibration event has occurred in the FID. Here, the method may include receiving a calibration log from the FID. The calibration log may describe an identifier of the FID, a scheduled date for the calibration of the FID, a scheduled time for the calibration of the FID, a date in which the calibration of the FID was performed, a time in which the calibration of the FID was performed, a gas supplied during the calibration, a gas concentration level supplied during the calibration, a raw count received during the calibration, and the like. The method may then compare the scheduled date with the date in which the FID was calibrated. If the scheduled date does not match the date in which the FID was calibrated, the method may display a message describing a missed calibration.

In yet another implementation, managing the validation of a FID calibration may include a method for determining whether a validation event has occurred in the FID. As such, the method may receive a validation log from the FID. The validation log may list an identifier of the FID, a scheduled date for the validation of the FID, a scheduled time for the validation of the FID, a date in which the validation of the FID was performed, a time in which the validation of the FID was performed, a gas supplied during the validation, a gas concentration level supplied during the validation, a raw count received during the validation, and the like. The method may then compare the scheduled date with the date in which the FID was validated. If the scheduled date does not match the date in which the FID was validated, the method may then display a message describing a missed validation.

In still another implementation, managing the calibration of a FID may include a method for storing a record about a maintenance performed on the FID. Here, the method may include receiving information about one or more scheduled maintenances to be performed on the FID and receiving a record about the maintenance performed on the FID. After receiving the information and record about the maintenance, the method may then store the record and the information on a maintenance log and send the maintenance log to the FID.

In yet still another implementation, managing the calibration or validation of the FID may include a method for initializing the FID. The method may include sending a first ignition command to the FID to ignite a first ignition source located in a chamber of the FID. After sending the first ignition command, the method may receive a first temperature value of the chamber from a temperature sensor disposed inside the chamber after a predetermined amount of time. If the first temperature value is less than the predetermined temperature value, the method may then include sending a second ignition command to the FID to ignite a second ignition source located in the chamber.

In yet another implementation, a system for managing the calibration of the FID may include a FID and a computer device in communication with the FID. The FID may have a first ignition source and a second ignition source located in a chamber of the FID. The FID may also have a temperature sensor for measuring the temperature inside the chamber. The computer device may include a processor and a memory with program instructions executable by the processor to send a first ignition command to the FID to ignite the first ignition source. The processor may then receive a first temperature value of the chamber from the temperature sensor after a predetermined amount of time. If the first temperature value is less than the predetermined temperature value, the processor may send a second ignition command to the FID to ignite the second ignition source.

In yet another implementation, managing the calibration of a FID may include a method for validating the calibration of the FID. Here, the method may include receiving a request to schedule a validation of the calibration. After receiving the request to schedule the validation, the method may send a flow request command to a gas distribution system to provide a gas at a gas concentration level to the FID at a scheduled validation time. The method may then receive a raw count from the FID. After the raw count is received, the method may determine whether the FID passes the validation. The method may then store the validation result in a validation log.

The above referenced summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

Implementations of various technologies will hereafter be described with reference to the accompanying drawings. It should be understood, however, that the accompanying drawings illustrate only the various implementations described herein and are not meant to limit the scope of various technologies described herein.

DETAILED DESCRIPTION

The discussion below is directed to certain specific implementations. It is to be understood that the discussion below is only for the purpose of enabling a person with ordinary skill in the art to make and use any subject matter defined now or later by the patent "claims" found in any issued patent herein.

The following paragraphs provide a brief executive summary of one or more implementations of various techniques directed to automatically managing the calibration and validation of a flame ionization detector (FID). In one implementation, the FID calibration and validation management system may include a FID, a Personal Digital Assistant (PDA), a gas distribution system, and a supply of one or more gases.

In operation, an operator may schedule one or more FIDs to be calibrated from a list of FIDs connected to a PDA. The schedule may provide for daily, weekly, or monthly calibrations for some or all of the connected FIDs. The operator may select a set of gases and gas concentration levels for each FID to be calibrated to.

Automatic Calibration

In general, calibration involves providing a gas, e.g., methane, at a specific concentration level into the FID. In one implementation, the FID calibration system may include a FID and a gas distribution system in communication with the PDA. The gas distribution system may provide the gas at a specific concentration level to the FID.

The PDA may be set to send a signal to the FID for any type of calibration (e.g., daily, precision or drift), which may automatically be performed at a predetermined time. At the predetermined time, the PDA may send a signal to the FID to ignite its ignition source, monitor/confirm the FID's warm-up time, administer calibration gases, perform electronic calibration, test and store all results. The results may be stored in the FID, PDA, and may also be transferred to a computer.

Failsafe Calibration

The PDA may compare an internal calendar with its calibration records and display a notice to the operator when any calibration event (such as daily calibration, quarterly precision calibration or periodic drift assessment) was required but has not been performed. The operator would have the option of setting a calibration requirement in the PDA, overriding the failsafe notice, or disabling other features of the FID until the calibrations are performed. This may provide an assurance that an operator may not inadvertently use a FID that has not been properly calibrated.

Automatic Backup Ignition & Ignition Failure Notice

At the scheduled calibration time, the PDA may send a signal to the FID to ignite its primary ignition source to initiate the warm up period for the FID. If the FID does not heat up to a predetermined temperature value within a certain period of time, the FID may send a failure notification to the PDA. This failure notification may alert the operator to repair the FID's primary ignition source. This failure notification may be displayed repeatedly until repair to the primary ignition source has been completed. The failure notification may also trigger the PDA to send an ignition command to the FID's backup ignition source.

Storing Calibration Log on PDA

The FID may generate a raw "count" from the gas provided by the gas distribution system and send the result back to the PDA. The PDA may correlate the supplied gas and its concentration level with the resulting "count" detected by the FID. The correlation may be compiled into a calibration log, which may be stored on the PDA. The calibration log may also be forwarded to the FID which may later forward the calibration log to a monitoring PDA and a main computer. The calibration log may also include an identifier of the supplied gas, the gas concentration level amount, the FID's raw count, and a date indicating when the calibration took place.

Automatic Validation

In one implementation, the operator may also schedule a time for validating the calibration. For instance, the validation of the calibration may be scheduled to immediately follow the calibration process. As such, after completing the calibration process, the FID may be validated to ensure proper detection. Here, the gas distribution system may again provide the gas at the specified concentration level to the FID. The PDA may receive the resultant count from the FID. A gas concentration level may be computed using the existing calibration log. The calibration of the FID detector may be validated by verifying that the gas concentration level amount provided by the gas distribution system is within a predetermined tolerance of the gas concentration level detected by the FID. Readings within the predetermined tolerance may indicate that the FID passes the validation process.

In one implementation, the validation may be based on an average of detected gas concentration levels over several trials. In another implementation, the validation may be based on how much time it takes for the FID detectors to detect the gas concentration level and send the relevant data to the PDA.

Wireless Interface

In one implementation, the FID takes most or all of its input and presents most or all of its output through a wireless interface to the PDA. As such, in this implementation, the FID has few, if any, buttons, displays, switches, keypads or physical interface. This enables the FID to be smaller, lighter, less susceptible to breakage, less expensive and easier to modernize and upgrade.

Storing Maintenance Records on FID

All maintenance records, including repair records, maintenance checks, replacement parts, confirmation of flow rates, quarterly calibration records, battery replacement, and the like, will be stored directly in the FID's onboard computer and in the memory of the PDA. This will enable the owner to have a ready source of all maintenance that has been performed on each FID for its entire lifetime.

FID's Capability to Interface With Multiple PDAs

The FID may be designed to interface with a wide variety of PDAs. This feature may give the owner the flexibility to operate the FID with a PDA that best suits the owner's other requirements.

PDA's Capability To Display Maintenance Needs and Schedules

The PDA may automatically display notices indicating a system malfunction or when a routine or periodic maintenance is required on a FID.

One or more implementations of various techniques in connection with the use of a FID will now be described in more detail with reference to FIGS. 1-5 in the following paragraphs.

Figure 1:
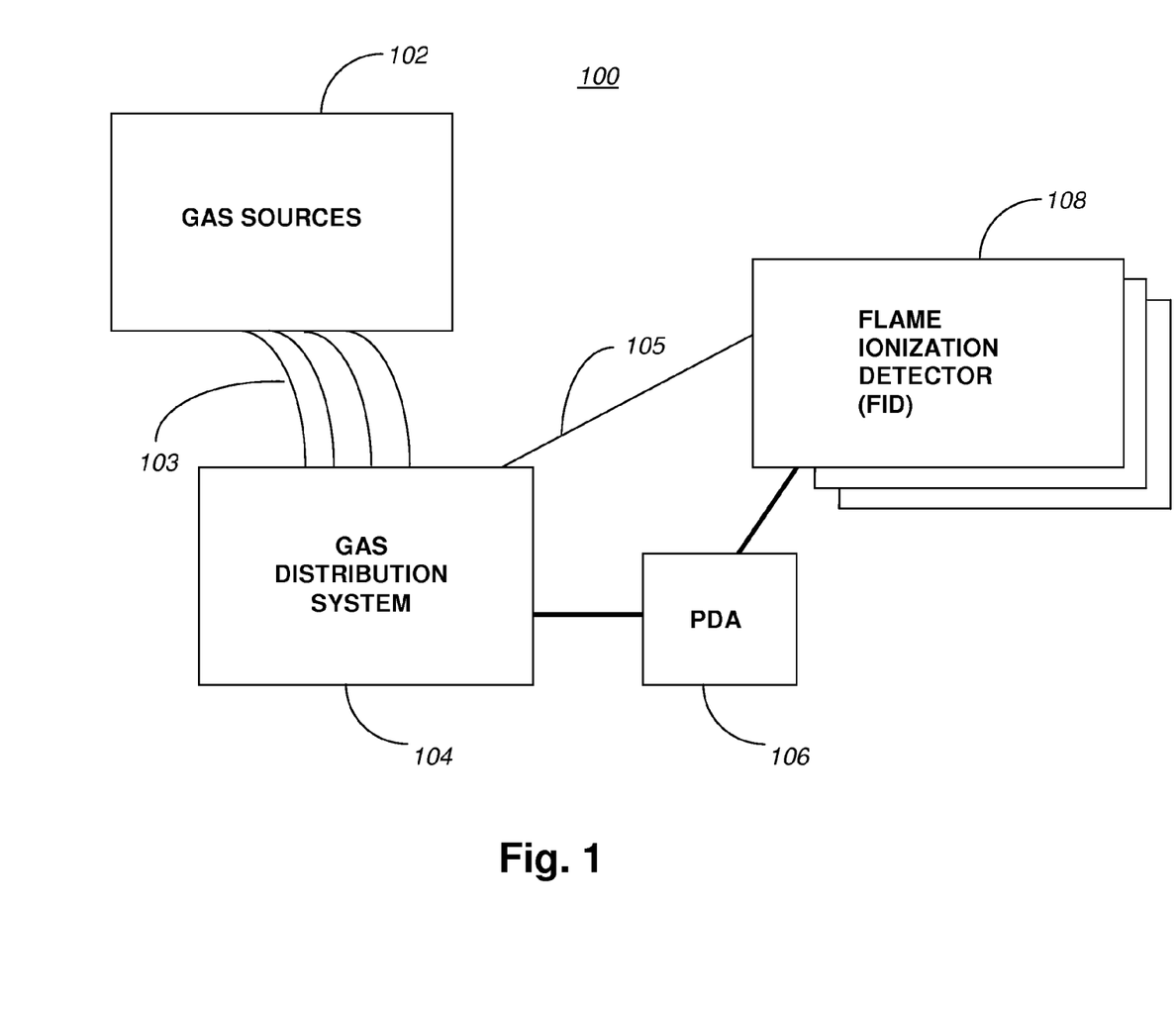
FIG. 1 illustrates a schematic diagram of a FID calibration system in accordance with one or more implementations of various technologies described herein.

FIG. 1 illustrates a schematic diagram of a FID calibration system 100 in accordance with one or more implementations of various technologies described herein. The calibration system 100 may include one or more gas sources 102, a gas distribution system 104, a PDA 106, and one or more FIDs 108.

The gas sources 102 may be configured to provide one or more gases to the calibration system 100. The gas sources 102 may provide different concentrations of gas through different gas lines 103 to the gas distribution system 104. For example, the gas sources 102 may provide a methane gas with a concentration of 100 parts-per-million (PPM) over a first gas line, a concentration of 550 PPM over a second gas line, 750 PPM over a third gas line, etc. Although various implementations described herein are with reference to methane gas, it should be understood that in some implementations, other types of gas may be used, such as hexane, propane, carbon tetrachloride, and the like.

The gas distribution system 104 may be configured to facilitate the delivery of gas to the FID 108. The gas distribution system 104 may also be referred to as a span box. The gas distribution system 104 may provide a specific gas concentration to the FID 108 by routing the gas from one of the gas lines 103 to the FID 108 through a FID gas line 105.

Further, although various implementations are described with reference to a gas distribution system 104 providing gas to the FID 108, it should be understood that in some implementations, the gas may be delivered directly to the FID 108 without use of a gas distribution system 104. For example, the delivery of the gas to the FID 108 may be performed manually, using bags, containers, and the like.

The PDA 106 may be in communication with the gas distribution system 104 and the FIDs 108. In one implementation, the gas distribution system 104 may be coupled to the PDA 106. Here, the gas distribution system 104 and the PDA 106 may communicate with each other via a shared processor. Communication between the PDA 106 and the gas distribution system 104 or the FIDs 108 may occur over wired or wireless connections. In one implementation, the PDA 106 may communicate with the gas distribution system 104 and the FIDs 108 via Bluetooth communications. Although various implementations described herein are with reference to Bluetooth communications, it should be understood that in some implementations, other types of communication methods may be used, such as serial cable, Ethernet cable, the Internet, and the like. The PDA 106 will be described in more detail in FIG. 2.

The FIDs 108 may be configured to detect volatile organic chemicals, emissions gases, nitro-aromatics, chemical warfare agents and the like. In one implementation, the FIDs 108 may use a battery power source so that the FID 108 may be easily transported to different locations. Further, the FID 108 may not include a video display or any other input/output peripherals, thereby decreasing the size of the FID 108. However, it should be understood that some implementations may provide options for various input/output modules and/or power sources. The FID 108 will be described in more detail in FIG. 3.

Figure 2:
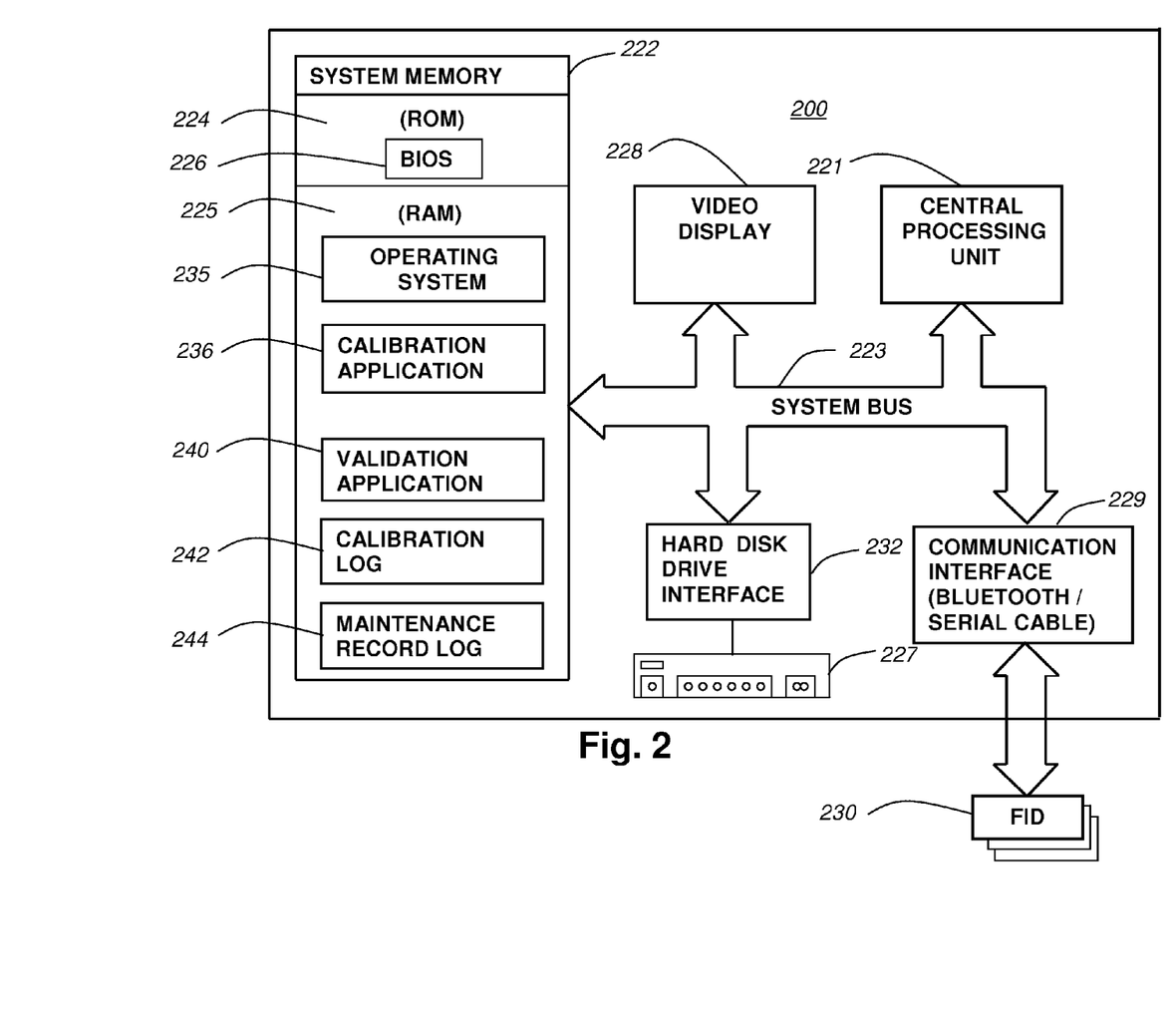
FIG. 2 illustrates a schematic diagram of a personal digital assistant (PDA) in accordance with one or more implementations of various technologies described herein.

FIG. 2 illustrates a schematic diagram of a PDA 200 in accordance with one or more implementations of various technologies described herein. The PDA 200 may include a central processing unit (CPU) 221, a system memory 222 and a system bus 223 that couples various system components including the system memory 222 to the CPU 221. Although only one CPU is illustrated in FIG. 2, it should be understood that in some implementations the PDA 200 may include more than one CPU. The system bus 223 may be any of several types of bus structures, including a memory bus or memory controller, a peripheral bus, and a local bus using any of a variety of bus architectures. By way of example, and not limitation, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. The system memory 222 may include a read only memory (ROM) 224 and a random access memory (RAM) 225. A basic input/output system (BIOS) 226, containing the basic routines that help transfer information between elements within the PDA 200, such as during start-up, may be stored in the ROM 224. A video display 228 or other type of display device may also be connected to system bus 223 via an interface, such as a video adapter.

The PDA 200 may further include a hard disk drive 227 for reading from and writing to a hard disk. The hard disk drive 227 may be connected to the system bus 223 by a hard disk drive interface 232. The drives and their associated computer-readable media may provide nonvolatile storage of computer-readable instructions, data structures, program modules and other data for the PDA 200.

The PDA 200 may include computer-readable media that may be accessed by the CPU 221. For example, such computer-readable media may include computer storage media and communication media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the CPU 221.

The PDA 200 may contain a communications interface 229 that may be used to connect with other FIDs 230. As mentioned above, PDA 200 may interface with FIDs 230 via Bluetooth communications. As such, the communications interface 229 may be a wireless communications interface. However, it should be understood that in some implementations the PDA 200 may use other types of communications methods.

Communication media may embody computer readable instructions, data structures, program modules or other data in a modulated data signal, such as a carrier wave or other transport mechanism and may include any information delivery media. The term "modulated data signal" may mean a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. Combinations of any of the above may also be included within the scope of computer readable media.

A number of program modules may be stored on ROM 224 or RAM 225, including an operating system 235, a calibration application 236, and a validation application 240. The operating system 235 may be any suitable operating system that may control the operation of a networked personal or server computer, such as Windows® XP, Mac OS® X, Unix-variants (e.g., Linux® and BSD®), and the like. The calibration application 236 will be described in more detail with reference to FIG. 4 in the paragraphs below. The validation application 240 will be described in more detail with reference to FIG. 5 in the paragraphs below. A calibration log 242 and a maintenance record log 244 may be stored on RAM 225, hard disk drive 227, or any other type of memory. The calibration log 242 and the maintenance record log 244 will be described in more detail with reference to FIG. 3 in the paragraphs below.

Although implementations of various technologies described herein are described with reference to a PDA 106, it should be understood that some implementations may be operational with other types of computing systems, such as laptop devices, tablet PCs, personal computers, multi-processor systems, microprocessor-based systems, programmable consumer electronics, minicomputers, and the like.

Figure 3:
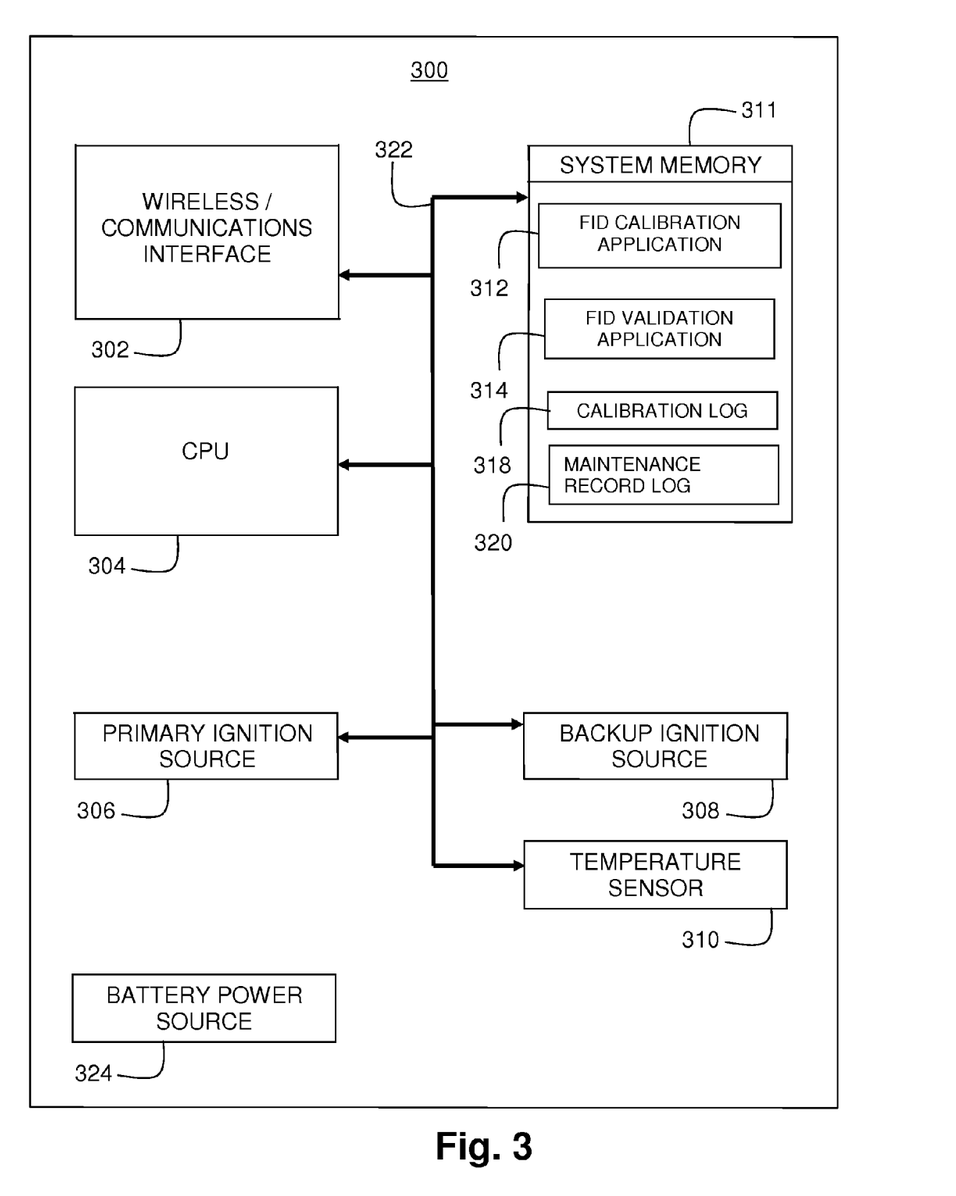
FIG. 3 illustrates a schematic diagram of a flame ionization detector (FID) device in accordance with implementations of various technologies and techniques described herein.

FIG. 3 illustrates a schematic diagram of a FID 300 in accordance with one or more implementations of various technologies described herein. The FID 300 may include a central processing unit (CPU) 304, a system memory 311, and a system bus 322 that couples the CPU 304 with various system components, including the system memory 311, a wireless communications interface 302, a temperature sensor 310, a primary ignition source 306, and a backup ignition source 308. The FID 300 may also include a battery power source 324 to provide power to the FID 300. In one implementation, the FID 300 may include a continuous power source as opposed to a battery power source 324.

In one implementation, the FID 300 takes most or all of its input and presents most or all of its output through the wireless communications interface 302 to one or more PDAs. As shown in FIG. 3, the wireless communications interface 302 is integrated with the FID 300. The wireless communications interface 302 may include a receiver, a transceiver or any other device that would enable the FID 300 to communicate wirelessly with the PDA. In one implementation, the wireless communications interface 302 may include a wireless chip. The wireless communication facilitated by the wireless communications interface 302 may be Bluetooth, WiFi, FM and the like. As such, the wireless communications interface 302 enables the FID 300 to communicate wirelessly with the PDA without the use of an adapter. Although the FID 300 has been described to communicate with other devices using a wireless communications interface, it should be noted that the FID 300 may also be capable of communicating with other devices via a wired communications interface as well.

A number of program modules may be stored on the system memory 311 including the FID calibration application 312 and the FID validation application 314. Each of these program modules will be described in more detail with reference to FIGS. 3-4 in the paragraphs below. In addition to the program modules stored on the system memory 311, the FID 300 may also store the calibration log 318 and the maintenance record log 320 in the system memory 311. The calibration log 318 may include information pertaining to the one or more calibrations that may have been performed on the FID 300. The information in the calibration log 318 may include the time and date of a calibration, the gas used in each calibration, the gas concentration level used for each calibration, and the raw count received for each gas and its corresponding gas concentration level. The maintenance log 320 may include information about one or more maintenance operations that may have been performed by the operator. The information in the maintenance log 320 may include a record listing one or more parts of the FID 300 that may have been replaced or repaired, a list of any maintenance performed on the FID 300, or the like. Although the calibration log 318 and the maintenance log 320 have been described to be stored in the system memory 311, it should be understood that the logs may be stored on an internal or external memory device that may not be included in this schematic.

It should be also understood that the various technologies described herein may be implemented in connection with hardware, software or a combination of both. Thus, various technologies, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the various technologies. In the case of program code execution on programmable computers, the computing device may include a processor, a storage medium readable by the processor (including volatile and non-volatile memory and/or storage elements), at least one input device, and at least one output device. One or more programs that may implement or utilize the various technologies described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

For example, the various technologies described herein may be implemented in distributed computing environments where tasks are performed by remote processing devices that are linked through a communications network, e.g., by hardwired links, wireless links, or combinations thereof. In a distributed computing environment, program modules may be located in both local and remote computer storage media including memory storage devices.

Figure 4:
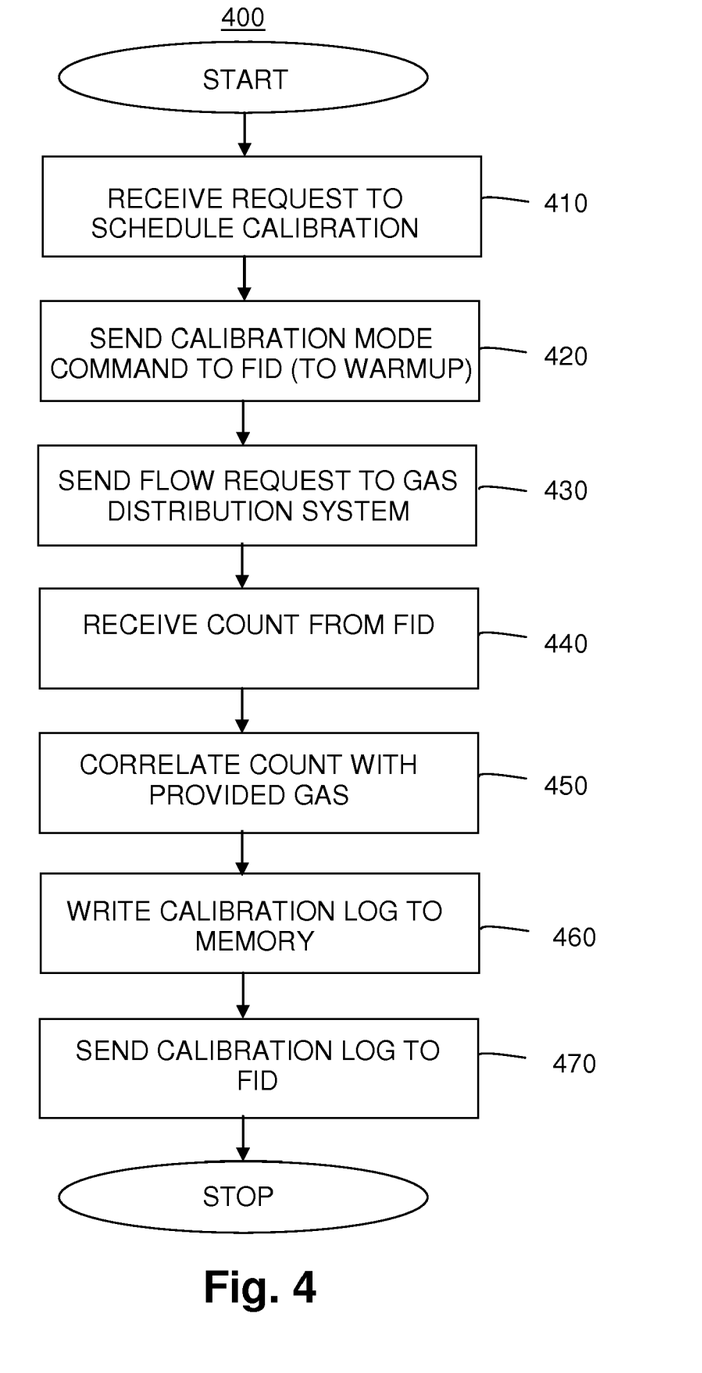
FIG. 4 illustrates a flow diagram of a method for calibrating a FID in accordance with implementations of various technologies and techniques described herein.

FIG. 4 illustrates a flow diagram of a method 400 for calibrating a FID in accordance with implementations of various technologies and techniques described herein. It should be understood that while the flow diagram indicates a particular order of execution of the operations, in some implementations, the operations might be executed in a different order. In one implementation, method 400 may be performed by the calibration program 236.

At step 410, the calibration application 236 may receive a request to schedule a calibration for one or more FIDs 108 that may be connected to the PDA 106. In one implementation, the operator may schedule one or more dates and/or times in which the FID 108 may be calibrated by entering in one or more dates and/or times in which the calibrations may take place. The operator may schedule a calibration for every day or once a week. For example, the operator may schedule a calibration to occur every Friday for each FID 108 connected to the PDA 106. The calibration application 236 may also receive a gas type and a corresponding gas concentration level to be used for the scheduled calibration. Accordingly, the operator using the PDA 106 may select one or more of the gas sources 102 and a corresponding gas concentration level to use for calibrating each FID 108 selected at step 410.

At step 420, at the scheduled time received at step 410, e.g., every Friday at 4:00 a.m., the calibration application 236 may send a calibration mode command to the FID 108 that may have been scheduled to be calibrated at step 410. The calibration mode command may trigger the FID calibration application 312 to initiate the calibration process for the FID 108 by sending a command to the primary ignition source 306 to ignite a flame within the chamber. After a predetermined period of time, the FID calibration application 312 may receive a temperature value of the chamber from the temperature sensor 310. In one implementation, the FID calibration application 312 may periodically receive the temperature value of the chamber from the temperature sensor 310. If the FID calibration application 312 receives a temperature value below a predetermined temperature value within a predetermined amount of time, the FID calibration application 312 may send a failure notification to the PDA 106. The failure notification may indicate that the primary ignition source 306 may require maintenance. In one implementation, in conjunction with sending the failure notification to the PDA 106, the FID calibration application 312 may also send a command to the backup ignition source 308 to ignite a flame within the chamber. Conversely, if the FID calibration application 312 receives a temperature value equal to or greater than a predetermined temperature value within a predetermined amount of time, the FID calibration application 312 may proceed to step 430.

In one implementation, the PDA 106 may receive the temperature value of the chamber from the FID 108. The calibration application 236 may determine whether the temperature value is below the predetermined value within the predetermined amount of time. If the calibration application 236 determines that the temperature value is below the predetermined value within the predetermined amount of time, the calibration application 236 may display a failure notification on the video display 228 and it may send a command to the FID calibration application 312 to ignite the backup ignition source 308.

In one implementation, the failure notification may display a recurring message on the video display 228 of the PDA 106 to notify the operator that maintenance may be required on the primary ignition source of the FID 108. Although the failure notification has been described to be sent when the primary ignition source fails during the warm up period, it should be noted that the failure notification may also be sent if the primary or the secondary ignition source fails at any time. Further, although the automatic backup ignition process has been described above with reference to calibrating a FID, it should be understood that in some implementations the automatic backup ignition process may be used independently apart from calibrating the FID.

At step 430, after the FID 108 has successfully warmed up, the calibration application 236 may send a flow request to the gas distribution system 104. The flow request may include the gas type and a corresponding concentration level that has been specified in the calibration schedule request received in step 410. In response to the flow request, the gas distribution system 104 may provide the specified gas type with its specified gas concentration level to the FID 108.

At step 440, the FID calibration application 312 may determine a raw count, which may be an electronic signature (digital representation) or representation of the gas concentration level supplied to the FID 108 by the gas distribution system 104. In one implementation, the raw count may be derived after the FID 108 combusts the gas provided by the gas distribution system 104 in the chamber of the FID 108. The FID 108 may then send the derived raw count value to the PDA 106. In one implementation, if a raw count value is not received by the PDA 106, the calibration program 236 may display a notification on the video display 228 indicating the failed calibration of the FID 108.

At step 450, the calibration application 236 may correlate the raw count detected by the FID 108 with the type and concentration level of the gas supplied to the FID 108. The correlation may be stored in a calibration log 242. In one implementation, the calibration log 242 may also include an identifier of the FID 108, e.g., a serial number, and the date and time that the calibration took place.

At step 460, the calibration application 236 may write the calibration log 242 into the hard disk drive 227 or another memory component of the PDA 200.

At step 470, the calibration application 236 may send the calibration log 242 to the FID 300 and save the log in the system memory 318. The calibration log 242 may be sent to FID 108 via the communications interface 229 of the PDA 200. In one implementation, the calibration log 318 may also be stored in a separate database located on a server or another computer system. An advantage of storing the calibration log 318 in a digital format may include avoiding typical recordation errors that may otherwise incur regulatory sanctions.

In one implementation, the calibration application 236 may compare the scheduled calibration times received at step 410 with the performed calibration times as indicated in the calibration log 242. If the calibration log 242 indicates that a scheduled calibration event has not been performed, the calibration application 236 may display a failsafe notice of this discrepancy on the video display 228 of the PDA 106. In one implementation, the calibration application 236 may allow the operator to override the failsafe notice, or it may disable one or more functions of the FID 108 until the calibrations are performed.

In another implementation, the operator may keep a record of any maintenance performed on the FID 108 using the calibration application 236. The calibration application 236 may store the maintenance records on the maintenance record log 244. In addition to keeping maintenance records recorded by the operator, the calibration program 236 may automatically display notices indicating when the FID 108 may be in need of a routine or periodic maintenance check. In one implementation, the calibration application 236 may send the maintenance record log 244 to the FID 108 for other operators to download.

Figure 5:
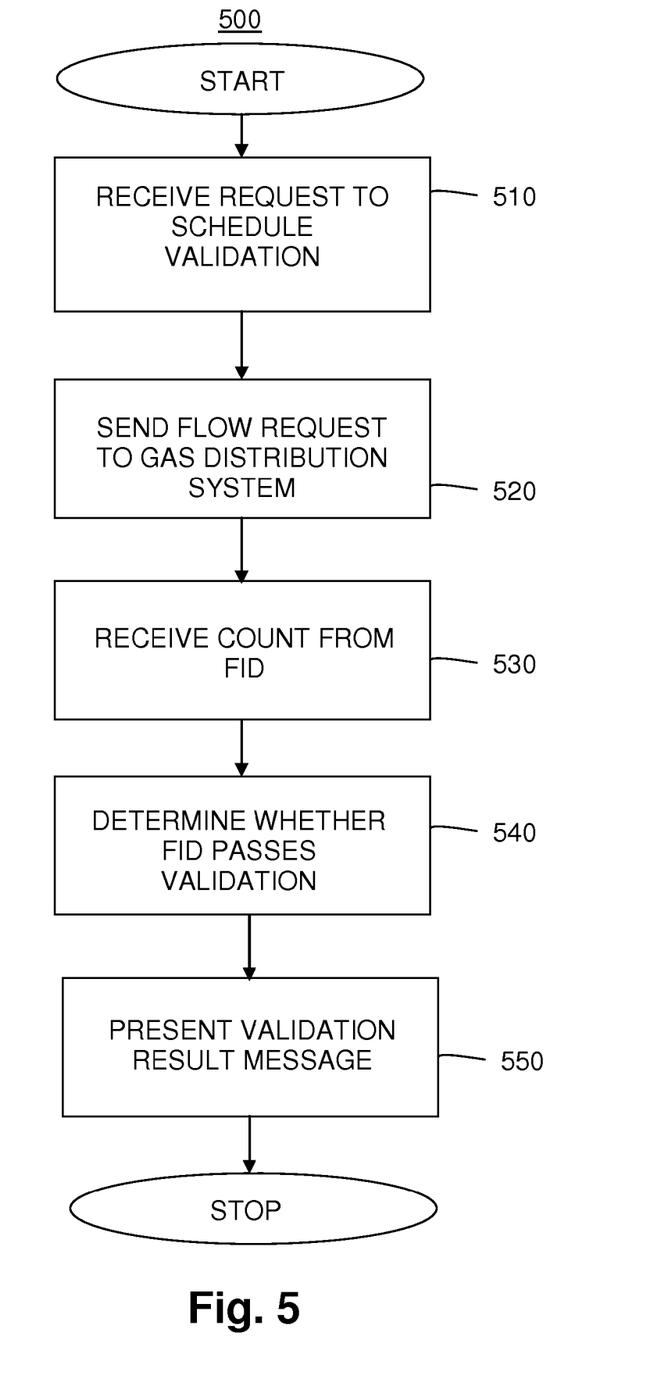
FIG. 5 illustrates a flow diagram of a method for validating the calibration of a FID in accordance with one or more implementations of various technologies and techniques described herein.

FIG. 5 illustrates a flow diagram of a method 500 for validating the calibration of the FID 108 in accordance with implementations of various technologies and techniques described herein. It should be understood that while the flow diagram indicates a particular order of execution of the operations, in some implementations, the operations might be executed in a different order. In one implementation, method 500 may be performed by the validation application 240. In one implementation, the validation application 240 may perform a validation test to validate the calibration of the FID 108.

At step 510, the validation application 240 may receive a request to schedule a time in which to validate the calibration of the FID 108. In one implementation, the scheduled time to validate the calibration of the FID 108 may be shortly after the scheduled time for calibration. The validation request may also specify a gas and a corresponding concentration level to be used for validating the calibration of the FID 108.

At step 520, the validation application 240 may send a flow request to the gas distribution system 104. The flow request may include the gas type and the corresponding concentration level amount specified in the scheduled validation request in step 510. In response to receiving the flow request, the gas distribution system 104 may provide the specified gas type at the specified gas concentration level to the FID 108. In one implementation, after the gas distribution system 104 provided the gas to the FID 108, the FID validation application 314 may determine a raw count representing a gas concentration level. The FID validation application 314 may then send the raw count to the PDA 106.

At step 530, the validation application 240 may receive the raw count from the FID validation application 314. In one implementation, the validation program 240 may convert the raw count received from the FID 108 into a gas concentration level using the data stored in the calibration log 242.

At step 540, the validation application 240 may determine whether the FID 108 passes the validation test. In one implementation, the validation application 240 may verify that the raw count received at step 530 matches the raw count listed in the calibration log 242 for the gas and gas concentration level supplied to the FID 108 at step 520. If the raw count received at step 530 and the raw count value listed in the calibration log is within a specified tolerance of each other, the validation application 240 may determine that the FID 108 has passed the validation test.

In another implementation, the validation application 240 may determine the gas and gas concentration level supplied to the FID 108 during calibration using the information in the calibration log. The validation application 240 may compare the raw count value received at step 530 to the raw count values listed in the calibration log. In one implementation, the validation application 240 may search for a raw count value in the calibration log that is within a specified tolerance of the raw count value received at step 530. If the validation application 240 finds a matching raw count value, it may determine that the received raw count correlates to the gas and gas concentration level as described in the calibration log for the same raw count. If the identified gas and gas concentration levels match the actual gas and gas concentration level provided to the FID 108 by the gas distribution system 104, it may be determined that the FID 108 has passed the validation test.

In addition to comparing the identified gas levels and the actual gas levels, the validation application 240 may also factor in the amount of time that passed between when the PDA 106 sent a flow request to the gas distribution system 104 and when the raw count was received from the FID validation application 314. In one implementation, the validation application 240 may validate the FID 108 by determining whether the gas concentration level detected by the FID validation application 318 is within a specified tolerance of the supplied gas concentration level and if the raw count was received by the validation application 240 within a specified amount of time. The specified tolerance may be a range of gas concentration close to the actual gas concentration value supplied to the FID 108. In one implementation, the FID 108 may be validated multiple times. Here, an average of the variances between the detected gas concentration levels and the supplied gas concentration levels may be calculated and used to validate the calibration of the FID 108.

At step 550, the validation application 240 may present the results of the validation on the video display 228 of the PDA 106. In one implementation, if the FID 108 passes the validation test, the validation program 240 may present a validation success message. If the FID 108 does not pass the validation test, the validation program 240 may present a validation failure message. In either event, the results of the validation may be stored on the memories of the FID 108 and the PDA 106.

In one implementation, the validation program 240 may store the result of each validation test in a log such as the calibration log 242. The stored result may also include an identifier of the FID 108 validated, the concentration level of the gas provided for the validation test, the corresponding gas concentration level detected by FID 108, and a date and/or time of the validation.

While the foregoing is directed to implementations of various technologies described herein, other and further implementations may be devised without departing from the basic scope thereof, which may be determined by the claims that follow. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for calibrating a flame ionization detector (FID), comprising: receiving one or more scheduled times for calibration;
sending a first ignition command to the FID to ignite a first ignition source located in a chamber of the FID;
receiving a first temperature value of the chamber;
determining whether the first temperature value is equal to or greater than a predetermined temperature value;
sending one or more flow request commands to a gas distribution system to provide a gas at a gas concentration level to the FID at the scheduled times if the first temperature is equal to or greater than the predetermined temperature value;
receiving one or more raw counts from the FID;
determining one or more correlations between the raw counts, the gas and the gas concentration level provided to the FID; and storing the correlations in a calibration log.

2. The method of claim 1, wherein the raw counts represent the gas concentration level.

3. The method of claim 1, further comprising sending the calibration log to the FID.

4. The method of claim 3, wherein the flow request commands and the calibration log are sent via a wireless communications interface.

5. The method of claim 1, further comprising:
receiving the gas to use during the calibration and the gas concentration level of the gas to use during the calibration.

6. The method of claim 1, further comprising: sending a second ignition command to the FID to ignite a second ignition source located in the chamber of the FID if the first temperature value is less than the predetermined temperature value;
receiving a second temperature value of the chamber;
determining whether the second temperature value is equal to or greater than the predetermined temperature value; and
sending the flow request commands to the gas distribution system if the second temperature value is equal to or greater than the predetermined temperature value.

7. The method of claim 6, further comprising displaying a message describing a failure of the first ignition source.

8. The method of claim 6, further comprising displaying a message describing a failure of the second ignition source if the second temperature value is not equal to or greater than the predetermined temperature value.

9. The method of claim 1, wherein the calibration log comprises an identifier of the FID, a scheduled date for the calibration of the FID, a scheduled time for the calibration of the FID, a date in which the calibration of the FID was performed, a time in which the calibration of the FID was performed, the gas supplied during the calibration, the gas concentration level supplied during the calibration, the raw counts received during the calibration, or combinations thereof.

10. The method of claim 9, further comprising:
comparing the scheduled date and time with the date and time in which the FID was calibrated; and
displaying a message describing a missed calibration if the scheduled date and time do not match the date and time in which the FID was calibrated.

11. The method of claim 9, further comprising:
comparing the scheduled date with the date in which the FID was calibrated; and
displaying a message describing a missed calibration if the scheduled date does not match the date in which the FID was calibrated.

12. The method of claim 1, further comprising displaying a message describing a failure in the calibration of the FID if the raw counts are not received.

13. The method of claim 1, further comprising:
receiving a record about a maintenance performed on the FID;
receiving information about one or more scheduled maintenances to be performed on the FID;
storing the record and the information on a maintenance log; and
sending the maintenance log to the FID.

14. The method of claim 13, further comprising displaying a notice when the scheduled maintenances are not performed.

15. The method of claim 1, further comprising displaying a notice when a periodic maintenance on the FID is required.

16. A method for validating a calibration of a flame ionization detector (FID), comprising:
receiving one or more scheduled times for a validation of the calibration; automatically sending one or more flow request commands to a gas distribution system to provide a gas at a gas concentration level to the FID at the one or more scheduled times;
receiving one or more raw counts from the FID;
determining whether the FID passes the validation;
storing a validation result in a validation log, wherein the validation log comprises an identifier of the FID, a scheduled date for the validation, a scheduled time for the validation, a date in which the validation was performed, a time in which the validation was performed, the gas supplied during the validation, the gas concentration level supplied during the validation, the raw counts received during the validation, or combinations thereof;
comparing the scheduled date and time with the date and time in which the validation was performed; and
displaying a message describing a missed validation if the scheduled date and time do not match the date and time in which the validation was performed.

17. The method of claim 16, wherein the raw counts represent the gas concentration level.

18. The method of claim 16, further comprising sending the validation log to the FID.

19. The method of claim 16, further comprising:
receiving the gas to use during the validation and the gas concentration level of the gas to use during the validation.

20. The method of claim 16, further comprising displaying a message describing a failure in the validation of the FID if the raw counts were not received.

21. The method of claim 16, wherein determining whether the FID passes the validation comprises:
identifying an expected raw count for the gas and the gas concentration level according to a calibration log;
comparing the expected raw count with the raw count received from the FID; and
determining that the FID passes the validation if the expected raw count matches the raw count within a specified tolerance.

22. A system, comprising:
a flame ionization detector (FID) comprising:
a first ignition source and a second ignition source located in a chamber of the FID; and
a temperature sensor for measuring a temperature inside the chamber; and
one or more computer devices in communication with the FID, wherein each computer device comprises:
a processor; and
a memory comprising program instructions executable by the processor to:
send a first ignition command to the FID to ignite the first ignition source;
receive a first temperature value of the chamber from the temperature sensor after a predetermined amount of time; and
send a second ignition command to the FID to ignite the second ignition source if the first temperature value is less than the predetermined temperature value.

23. The system of claim 22, wherein the memory further comprises program instructions executable by the processor to display a message describing a failure of the first ignition source.

24. The system of claim 22, wherein the memory further comprises program instructions executable by the processor to:

receive a second temperature value of the chamber from the temperature sensor after the predetermined amount of time;

determine whether the second temperature value is equal to or greater than the predetermined temperature value; and display a message describing a failure of the second ignition source if the second temperature value is less than the predetermined temperature value.

25. The system of claim 22, wherein the memory comprises records of the calibration of the FID, the validation of the FID, the maintenance of the FID, or combination thereof.

26. The system of claim 22, further comprising a battery power source configured to power the FID.

27. A method for initializing a flame ionization detector (FID), comprising:
sending a first ignition command to the FID to ignite a first ignition source located in a chamber of the FID;
receiving a first temperature value of the chamber from a temperature sensor disposed inside the chamber after a predetermined amount of time; and
sending a second ignition command to the FID to ignite a second ignition source located in the chamber if the first temperature value is less than the predetermined temperature value.

28. The method of claim 27, further comprising displaying a message describing a failure of the first ignition source.

29. The method of claim 27, further comprising:
receiving a second temperature value of the chamber from the temperature sensor after the predetermined amount of time;
determining whether the second temperature value is equal to or greater than the predetermined temperature value; and
displaying a message describing a failure of the second ignition source if the second temperature is less than the predetermined temperature value.

30. A method for determining whether a calibration event has occurred in a flame ionization detector (FID), comprising:
receiving a calibration log from the FID, wherein the calibration log comprises an identifier of the FID, a scheduled date for a calibration of the FID, a scheduled time for the calibration of the FID, a date in which the calibration of the FID was performed, a time in which the calibration of the FID was performed, a gas supplied during the calibration, a gas concentration level supplied during the calibration, a raw count received during the calibration, or combinations thereof;
comparing the scheduled date with the date in which the FID was calibrated;
displaying a message describing a missed calibration if the scheduled date does not match the date in which the FID was calibrated; and
displaying a notice when a periodic maintenance on the FID is required.

31. A method for determining whether a validation event has occurred in a flame ionization detector (FID), comprising:
receiving a validation log from the FID, wherein the validation log comprises an identifier of the FID, a scheduled date for the validation of the FID, a scheduled time for the validation of the FID, a date in which the validation of the FID was performed, a time in which the validation of the FID was performed, a gas supplied during the validation, a gas concentration level supplied during the validation, a raw count received during the validation, or combinations thereof;
comparing the scheduled date with the date in which the FID was validated; displaying a message describing a missed validation if the scheduled date does not match the date in which the FID was validated; and
displaying a notice when a periodic maintenance on the FID is required.

32. A method for storing a record about a maintenance performed on a flame ionization detector (FID), comprising:
receiving information about one or more scheduled maintenances to be performed on the FID;
receiving a record about the maintenance performed on the FID;
storing the record and the information on a maintenance log, wherein the maintenance log comprises one or more repair records, one or more maintenance checks, one or more replacement parts, one or more confirmations of flow rates, one or more battery replacements or combinations thereof; and
sending the maintenance log to FID;
displaying a notice when the scheduled maintenances are not performed; and
displaying a notice when a periodic maintenance on the FID is required.

33. A system, comprising: a flame ionization detector (FID); and one or more computer devices in communication with the FID, wherein each computer device comprises:
a processor; and
a memory comprising program instructions executable by the processor to:
receive one or more scheduled times for calibration;
send a first ignition command to the FID to ignite a first ignition source located in a chamber of the FID;
receive a first temperature value of the chamber;
determine whether the first temperature value is equal to or greater than a predetermined temperature value;
send one or more flow request commands to a gas distribution system to provide a gas at a gas concentration level to the FID at the scheduled times if the first temperature is equal to or greater than the predetermined temperature value;
receive one or more raw counts from the FID for the one or more scheduled times;
determine one or more correlations between the raw counts, the gas and the gas concentration level provided to the FID; and
store the correlations in a calibration log.

34. The system of claim 33, wherein the flame ionization detector comprises a battery power source configured to power the FID.

35. A system, comprising:
a flame ionization detector (FID); and
one or more computer devices in communication with the FID, wherein each computer device comprises:
a processor; and
a memory comprising program instructions executable by the processor to:
receive one or more scheduled times for a validation of a calibration;
send a first ignition command to the FID to ignite a first ignition source located in a chamber of the FID;
receive a first temperature value of the chamber;
determine whether the first temperature value is equal to or greater than a predetermined temperature value;
send one or more flow request commands to a gas distribution system to provide a gas at a gas concentration level to the FID at the scheduled times if the first temperature value is equal to or greater than the predetermined temperature value;

determine whether the FID passes the validation; and store a validation result in a validation log.

36. The system of claim 35, wherein the flame ionization detector comprises a battery power source configured to power the FID.

37. A non-transitory computer-readable medium having stored thereon computer-executable instructions which, when executed by a computer, cause the computer to:

receive one or more scheduled times for calibration;

send a first ignition command to a flame ionization detector (FID) to ignite a first ignition source located in a chamber of the FID;

receive a first temperature value of the chamber;

determine whether the first temperature value is equal to or greater than a predetermined temperature value;

send one or more flow request commands to a gas distribution system to provide a gas at a gas concentration level to the FID at the scheduled times if the first temperature value is equal to or greater than the predetermined temperature value;

receive one or more raw counts from the FID;

determine one or more correlations between the raw counts, the gas and the gas concentration level provided to the FID; and store the correlations in a calibration log.

38. A non-transitory computer-readable medium having stored thereon computer-executable instructions which, when executed by a computer, cause the computer to:

receive a calibration log from a flame ionization detector (FID), wherein the calibration log comprises an identifier of the FID, a scheduled date for the calibration of the FID, a scheduled time for the calibration of the FID, a date in which the calibration of the FID was performed, a time in which the calibration of the FID was performed, a gas supplied during the calibration, a gas concentration level supplied during the calibration, a raw count received during the calibration, or combinations thereof;

compare the scheduled date with the date in which the FID was calibrated;

display a message describing a missed calibration if the scheduled date does not match the date in which the FID was calibrated; and display a notice when a periodic maintenance on the FID is required.

39. A non-transitory computer-readable medium having stored thereon computer-executable instructions which, when executed by a computer, cause the computer to:

receive a validation log from a flame ionization detector (FID), wherein the validation log comprises an identifier of the FID, a scheduled date for the validation of the FID, a scheduled time for the validation of the FID, a date in which the validation of the FID was performed, a time in which the validation of the FID was performed, a gas supplied during the validation, a gas concentration level supplied during the validation, a raw count received during the validation, or combinations thereof;

compare the scheduled date with the date in which the FID was validated;

display a message describing a missed validation if the scheduled date does not match the date in which the FID was validated; and display a notice when a periodic maintenance on the FID is required.

40. A non-transitory computer-readable medium having stored thereon computer-executable instructions which, when executed by a computer, cause the computer to:

receive information about one or more scheduled maintenances to be performed on a flame ionization detector (FID);

receive a record about a maintenance performed on the FID;

store the record and the information on a maintenance log, wherein the maintenance log comprises one or more repair records, one or more maintenance checks, one or more replacement parts, one or more confirmations of flow rates, one or more battery replacements or combinations thereof;

send the maintenance log to the FID;

display a notice when the scheduled maintenances are not performed; and display a notice when a periodic maintenance on the FID is required.

41. A non-transitory computer-readable medium having stored thereon computer-executable instructions which, when executed by a computer, cause the computer to:

send a first ignition command to a flame ionization detector (FID) to ignite a first ignition source located in a chamber of the FID;

receive a first temperature value of the chamber from a temperature sensor disposed inside the chamber after a predetermined amount of time; and send a second ignition command to the FID to ignite a second ignition source located in the chamber if the first temperature value is less than the predetermined temperature value.

42. A non-transitory computer-readable medium having stored thereon computer-executable instructions which, when executed by a computer, cause the computer to:

receive one or more scheduled times for a validation of a calibration; automatically send one or more flow request commands to a gas distribution system to provide a gas at a gas concentration level to a flame ionization detector (FID) at the one or more scheduled times;

receive one or more raw counts from the FID;

determine whether the FID passes the validation;

storing a validation result in a validation log, wherein the validation log comprises an identifier of the FID, a scheduled date for the validation, a scheduled time for the validation, a date in which the validation was performed, a time in which the validation was performed, the gas supplied during the validation, the gas concentration level supplied during the validation, the raw counts received during the validation, or combinations thereof;

comparing the scheduled date and time with the date and time in which the validation was performed; and displaying a message describing a missed validation if the scheduled date and time do not match the date and time in which the validation was performed.

* * * * *